US008673351B2

(12) United States Patent
Andrýsek et al.

(10) Patent No.: US 8,673,351 B2
(45) Date of Patent: Mar. 18, 2014

(54) CRYSTALLIZATION INHIBITOR AND ITS USE IN GELATIN CAPSULES

(75) Inventors: Tomáš Andrýsek, Branka u Opavy (CZ); Aleš Vrána, Opava (CZ)

(73) Assignee: Ivax Pharmaceuticals S.R.O., Opava (CZ)

( * ) Notice: Subject to any disclaimer, the term of this patent is extended or adjusted under 35 U.S.C. 154(b) by 556 days.

(21) Appl. No.: 11/886,500

(22) PCT Filed: Mar. 16, 2006

(86) PCT No.: PCT/US2006/009859
§ 371 (c)(1),
(2), (4) Date: Oct. 20, 2008

(87) PCT Pub. No.: WO2006/102157
PCT Pub. Date: Sep. 28, 2006

(65) Prior Publication Data
US 2011/0020438 A1     Jan. 27, 2011

Related U.S. Application Data

(60) Provisional application No. 60/664,826, filed on Mar. 21, 2005.

(51) Int. Cl.
*A61K 9/48*     (2006.01)

(52) U.S. Cl.
USPC ........................................... 424/452

(58) Field of Classification Search
None
See application file for complete search history.

(56) References Cited

U.S. PATENT DOCUMENTS

| | | | | |
|---|---|---|---|---|
| 4,388,307 | A * | 6/1983 | Cavanak | 514/20.5 |
| 4,888,239 | A * | 12/1989 | Brox | 428/402.2 |
| 5,441,738 | A | 8/1995 | Klein et al. | |
| 6,063,762 | A | 5/2000 | Hong et al. | |
| 6,267,985 | B1 * | 7/2001 | Chen et al. | 424/451 |
| 6,451,339 | B2 * | 9/2002 | Patel et al. | 424/451 |
| 6,696,482 | B2 * | 2/2004 | Shenoy et al. | 514/418 |
| 6,761,903 | B2 * | 7/2004 | Chen et al. | 424/451 |
| 2001/0012844 | A1 * | 8/2001 | Shenoy et al. | 514/259 |
| 2002/0032171 | A1 * | 3/2002 | Chen et al. | 514/54 |
| 2003/0235595 | A1 * | 12/2003 | Chen et al. | 424/400 |
| 2004/0009225 | A1 * | 1/2004 | Vanderbist et al. | 424/484 |
| 2004/0022862 | A1 * | 2/2004 | Kipp et al. | 424/490 |
| 2004/0033257 | A1 * | 2/2004 | Iyer et al. | 424/456 |
| 2004/0051192 | A1 * | 3/2004 | Suzuki et al. | 264/4.3 |
| 2004/0101552 | A1 * | 5/2004 | Patel | 424/450 |
| 2004/0102366 | A1 * | 5/2004 | Patel | 514/11 |
| 2005/0220825 | A1 | 10/2005 | Funke et al. | |

FOREIGN PATENT DOCUMENTS

| | | |
|---|---|---|
| EP | 0 327 280 A1 | 8/1989 |
| GB | 2 228 198 A | 8/1990 |
| GB | 2 282 586 A | 4/1995 |
| JP | 10211425 A * | 8/1998 |
| JP | 2000126586 A * | 5/2000 |
| WO | 9309211 A1 | 5/1993 |
| WO | WO-99/44584 A1 | 9/1999 |
| WO | WO-99/49848 A1 | 10/1999 |
| WO | WO-2004/073744 A1 | 9/2004 |
| WO | WO-2005/065652 A1 | 7/2005 |

OTHER PUBLICATIONS

Gursoy RN, Benita S. Self-emulsifying drug delivery systems (SEDDS) for improved oral delivery of lipophilic drugs. Apr. 2004, Biomed Pharmacother. 58(3):173-182.*

Reich, G. Formulation and physical properties of soft capsules. In: F. Podczek and B.E. Jones, Editors, Pharmaceutical Capsules, Pharmaceutical Press, London (2004), pp. 201-212.*

R Neslihan Gursoy, Simon Benita. Self-emulsifying drug delivery systems (SEDDS) for improved oral delivery of lipophilic drugs. Biomedicine & Pharmacotherapy vol. 58, Issue 3, Apr. 2004, pp. 173-182.*

Gabriele Reich. Formulation and physical properties of soft casules. in: Pharmaceutical capsules. Edited by Fridrun Podczeck and Brian E. Jones; (2004) Chapter 11:201-212.*

* cited by examiner

*Primary Examiner* — Robert A Wax
*Assistant Examiner* — Olga V Tcherkasskaya
(74) *Attorney, Agent, or Firm* — Kenyon & Kenyon LLP

(57) ABSTRACT

The present invention describes soft gelatin capsules that encapsulate a water-insoluble active ingredient and an excipient composed of a crystallization inhibitor that stabilizes the water-insoluble inhibitor. The crystallization inhibitor being at least one mononacylglycerol compound whose acyl group is a fatty acid residue of 6-18 carbon atoms. The capsule contents are more resistant to turbidity, forming a coarse emulsion, and crystallization of the active ingredient compared with compositions absent the crystallization inhibitor.

21 Claims, No Drawings

US 8,673,351 B2

CRYSTALLIZATION INHIBITOR AND ITS USE IN GELATIN CAPSULES

CROSS REFERENCE TO RELATED APPLICATIONS

The present application is a national phase entry under 35 U.S.C. §371 of International Application No. PCT/US2006/009859, filed Mar. 16, 2006, published in English, which claims benefit of U.S. Provisional Patent Application No. 60/664,826, filed Mar. 21, 2005. The disclosures of all of said applications are incorporated by reference herein.

FIELD OF THE INVENTION

The present invention relates to the stabilization of soft gelatin capsule compositions encapsulating emulsions of water-insoluble active substances and a crystallization inhibitor, wherein the crystallization inhibitor is a monoacylglycerol.

BACKGROUND OF THE INVENTION

Lachmann, in "Theory and Practice of Industrial Pharmacy", Lea and Febiger, Philadelphia, 2nd Edition, describes that there are three types of fill compositions that can be distinguished with regard to suitability for encapsulation into soft gelatin capsules:

1) Fill compositions whose major ingredients (e.g., excipient or solvent) are water-immiscible substances, such as oil, fat, essential (ethereal) oil, chlorohydrocarbons, esters, ethers, higher alcohols, and organic acids.
2) Fill compositions whose major ingredients are water-miscible, nonvolatile substances, such as polyethylene glycols or emulsifiers.
3) Fill compositions whose major ingredients are water-miscible, relatively volatile substances, such as glycerol, propylene glycol, and benzyl alcohol.

Fill compositions 2 and 3 are considered to be difficult to encapsulate. For example, Lachmann states that category 3 compositions, particularly those containing more than 5% of water and a low molecular, organic, water-soluble substance (e.g., ethanol, ketones, and amines) can not be encapsultated.

It is known that gels prepared from biological macromolecules (e.g., polysaccharides or proteins) undergo a phenomenon called syneresis. During this process, roughly speaking, a part of the water contained in the gel is forced out of the intermolecular space due to intramolecular and especially intermolecular hydrogen bonds which make macromolecular chains approach one another. As a result of this phenomenon, the water initially contained in the gel is forced out to the physical gel boundaries and passes to the surrounding environment. Soft gelatin capsules (i.e., capsules manufactured on an industrial scale that consist of a shell and a fill composition), wherein the shell is prepared from a gelatin gel and the fill composition contains an active ingredient (e.g., a medicinal, cosmetic, food product, or food additive), also undergo syneresis.

It is very difficult, for the above reasons, to prepare a soft gelatin capsule having a gelatin shell and a fill composition if the fill composition is of type 2 or 3. In addition, it can also be difficult if the fill composition, for reasons mentioned below, is incompatible with the amount of water that passes from the gelatin shell to the contents during the first few hours after encapsulation due to syneresis. Fill types 1 and 2 can be difficult to encapsulate into the gelatin shell due to water incompatibility because of one of the following grounds:

a. The capsule contents (i.e., fill) are hydrophobic and almost entirely immiscible with water. After the contents have been enclosed in a gelatin capsule, the capsule contents separate due to the water passing from the capsule into the contents. The water-insoluble substance can easily crystallize as a result.
b. The contents are hydrophobic (lipophilic) but contain surfactants (tensides), wherein the total HLB value of that composition is such that the composition is capable of absorbing (tolerating) some amount of water. However, the amount of water tolerable is generally less than the amount of water that passes into the contents due to syneresis. Thus, a W/O (water-in-oil) emulsion is produced, and the capsule contents become adversely turbid. The amount of water that passes from the shell to the capsule contents due to syneresis is usually 5 to 15% w/w. Turbidity occurs if the composition of the contents is capable of absorbing no more than 10 and especially no more than 5 wgt % of water without causing phase separation.
c. The contents are lipophilic but contain surfactants (tenides) of such a type and quantity that the contents could tolerate at least 5% or at least 10% w/w of water from syneresis. However, at least one of the essential ingredients of the contents shows such a low solubility in water that the capsules prepared are not stable.

Solutions for the problems associated with the above types of the contents intended for soft gelatin capsules include the following:

I. For the problem a (i.e., hydrophobic contents), full use is made of their absolute immiscibility with water due to which the aqueous phase that separates after encapsulation can resorb into the gelatin shell during the drying process of capsules. This method of solution is the subject of patent number EP 00671901.

II. For problem b, the amount of water that passes from the shell to the capsule contents is reduced by adding a water-binding substance to the gelatin composition. An example of this method of solution is provided in patent number U.S. Pat. No. 4,804,542. The water-binding substances may be, for instance, starch, cellulose, dry milk, non-hygroscopic mono-, di- and oligo-saccharides, magnesium silicate, silicon dioxide, and their mixtures. Alternatively, the composition can be changed so that the contents are absolutely immiscible with water, and thus transformed into the contents as described in item a) above (e.g., encapsulation of essential oil WO/95/09604, encapsulation of Sandimmun).

III. For problem c, substances are added to increase the water solubility of the essential ingredients of the contents. These substances include, for examples, polyvinyl pyrrolidines (Povidones, Kollidones), polyethoxylated sorbitols, and polyethylene glycols (see EP 0120248 B1).

There are a number of disadvantages of solutions I-III. First, if a fill composition is transformed into a solution that is totally immiscible with water, as described in solution I, the bioavailability of an active ingredient in the solution usually diminishes. It happens because transport through the intestinal cell membrane is possible only if the immiscible aqueous layer, adjoining the surface of intestinal epithelium and thus forming a hydrophilic barrier to the absorption of lipophilic substances, is permeated through. Second, from a purely practical standpoint, the addition of a water-binding substance to a gelatin composition (solution II) does not solve the problem of a the volume of water that passes from the gelatin gel into the capsule contents due to syneresis as the addition of any such water-binding substance requires the primary amount of water in a gelatin composition to be increased for the processing to be technically feasible. Third, the addition of substances that increase the solubility of a water-insoluble substance in water (solution III) almost always results in interaction with the shell and deterioration of the properties of the contents to be encapsulated.

Lachmann further notes that very low concentrations of hydrophilic surfactants (tensides) of polysorbate or Triton X-100 types can effectively slow down the growth of crystals in water. However, this effect proves to be ineffective with complex systems of the fill compositions intended for soft gelatin capsules. Moreover, the use of macromolecular additives that increase the viscosity of the contents seems to be ineffective as well because a pharmaceutical additive cannot be usually dissolved in the amphiphilic fill composition.

Importantly, the addition of pharmaceutical aids (e.g., solubilizers and surfactants) that increase the solubility of water insoluble substances is not always effective. A notable example of substances, showing such a low solubility in water that the above pharmaceutical aids are ineffective at increasing their water-solubility, are cyclosporines, i.e., cyclic undecapeptides. The pharmaceutical formulations of cyclosporines based on solvent systems consisting of a lipophilic ingredient (e.g., oil ingredient), a solvent (e.g., ethanol), and an amphiphilic ingredient that may have emulsifying properties (e.g., lecithin, and PEG) are characterized by the fact that they are not completely hydrophobic and are not totally immiscible with water. Their HLB value enables water to be absorbed up to a certain limit which is, however, less than the amount of water that passes from the shell to the contents of a gelatin capsule after encapsulation.

Other solutions to the above formulation problems are based on reducing the amount of water that passes to a gelatin composition either by decreasing the gelatin/contents weight ratio during encapsulation (by using the gelatin shell with a thin wall, etc.) or by partially replacing an amount of water in a gelatin composition with a larger amount of a plasticizer (e.g., glycerol, propylene glycol, sorbitol, etc, see GB 2282586), are accompanied by major technological problems. Simple reduction of the primary water content in a gelatin composition results in a necessity of processing a gelatin mixture with very high viscosity which has adverse effects on an encapsulation machine. The replacement of a large amount of water with a plasticizer results in the production of a gelatin mixture from which the strips of gelatin gel are prepared that show high adhesion and low melting point. The use of substances for forming a secondary gel matrix usually leads to the production of very soft capsules that easily fall apart.

It is desirable to find an appropriate substance, which would, at minimum or reasonable concentrations, increase the amount of water that can be absorbed (tolerated) by a composition, without causing phase separation (i.e., turbidity and/or formation of a coarse emulsion and/or crystallization of the water-insoluble component). The finding of an appropriate additive should also provide other benefits in some specific cases. For instance, with the fill compositions containing highly volatile substances, such as ethanol, a very intensive drying process can result in the loss of these volatile substances and a decrease in their concentration in the contents. An adverse consequence of a decrease in the concentration of the volatile substances below a critical limit is the instability of the contents caused by the crystallization of an active substance which was dissolved initially in the volatile substance. The appropriate additive could also help stabilize such compositions.

SUMMARY OF THE INVENTION

The present invention provides a gelatin capsule whose contents comprise a water-insoluble active ingredient (e.g., a medicinal product, cosmetic product, food, or food additive) and a crystallization inhibitor that helps stabilize the water-insoluble active ingredient and prevent turbidity, formation of a coarse emulsion, and/or crystallization of the active ingredient due to the presence of water from syneresis or other environmental changes inside the capsule.

The present invention also provides a method of making a gelatin capsule whose contents comprise a water-insoluble active ingredient and a crystallization inhibitor.

These and other advantages will become apparent during the following detailed description.

DETAILED DESCRIPTION OF THE INVENTION

The present invention provides a soft gelatin capsule that encapsulates difficult to encapsulate contents (e.g., see those described in problem b above), except that presence of water due to syneresis does not cause turbidity or the production of a coarse emulsion, and thus initiate the crystallization of the active substance. It has been discovered that if a crystallization inhibitor is added to the contents; they become stabilized, the clarity of the contents is maintained (i.e., no or limited turbidity), and a coarse emulsion is prevented from being produced. Additionally, if oil such as vegetable oil is used as an excipient to dissolve a water-insoluble active ingredient, then partial hydrophilization of the oil can be achieved.

The soft gelatin capsule of the present invention, comprises a gelatin shell and a capsule content, comprising: a water-insoluble active ingredient (see some examples below), which is dissolved in an excipient. The excipient comprises a crystallization inhibitor that is at least one monoacylglycerol. Typically, the acyl portion of the monoacylglycerol is a fatty acid residue consisting of 6, 7, 8, 9, 10, 11, 12, 13, 14, 15, 16, 17, to 18 carbon atoms. Residue refers to the acyl portion (i.e., the alkyl-carbonyl portion) of a fatty acid. As a result of the presence of the crystallization inhibitor, the present invention can provide stable, soft gelatin capsules comprising a water-insoluble ingredient. Examples of crystallization inhibitors include glycerol monooleate, glycerol monolinoleate, glycerol monopalmitate, glycerol monostearate, glycerol monolaurate, glycerol monocaprylate, glycerol monocaprate, and mixtures thereof. The crystallization inhibitor can be present in an amount of from 2, 3, 4, 5, 6, 7, 8, 9, to 10% w/w with respect to the weight of the contents. The crystallization inhibitor can also be more than one monoacylglycerol (e.g., 2 or 3).

Examples of fatty acids consisting of 6, 7, 8, 9, 10, 11, 12, 13, 14, 5, 16, 17, to 18 carbon atoms include oleic, linoleic, palmitic, stearic, lauric, caprylic, and caproic.

The excipient of the gelatin capsules of the present invention, in addition to the crystallization inhibitor (or inhibitors), can further comprise: (a) hydrophilic solvents (e.g., ethanol), (b) lipophilic solvents (e.g., a natural or synthetic oil additive such as corn oil or vegetable oil), (c) surfactants (e.g., lecithin, glyceryl macrogol esters of fatty acids or a vegetable, animal, or synthetic oil), and (d) lipophilic carriers. Surfactants are also termed amphiphilic materials and are well known in the art. Examples of the fatty acid portion of the glyceryl macrogol esters include fatty acids consisting of 6, 7, 8, 9, 10, 11, 12, 13, 14, 5, 16, 17, to 18 carbon atoms. The lipophilic carriers generally behave like lipophilic solvents; they help transport the active ingredient into the site of absorption. Examples of lipophilic carriers include di- or tri-esters of glycerol and fatty acids consisting of 6, 7, 8, 9, 10, 11, 12, 13, 14, 5, 16, 17, to 18 carbon atoms or their mixtures or di- or tri-esters of glycerol and an oil or a mixture of oils (e.g., vegetable oil, animal oil, or synthetic oil). Examples of the amounts of the ingredients in the excipient include ≤25% w/w hydrophilic solvents, ≥20% w/w lipophilic carriers, ≤50% w/w of surfactants whose HLB value is >11, and optionally antioxidants.

Examples of fatty acids consisting of 6, 7, 8, 9, 10, 11, 12, 13, 14, 5, 16, 17, to 18 carbon atoms include oleic, linoleic, palmitic, stearic, lauric, caprylic, and caproic.

The compositions of the present invention can be beneficial, in particular for such pharmacologically active substances that have low solubility in water and show their maximum bioavailability in solvent systems consisting of a lipophilic ingredient (e.g., oil ingredient), a solvent (e.g., ethanol), and a surfactant that may have emulsifying properties (e.g., lecithin, glyceryl macrogol esters of fatty acids or vegetable oils).

The capsule contents of the present invention are characterized by the fact that they are not completely hydrophobic and absolutely immiscible with water. On the contrary, their HLB value enables some amount of water entering the contents from syneresis to be absorbed up to a certain limit concentration. This concentration will often times be lower than that actual amount of water that passes from the shell to the contents after encapsulation. It is expected that the contents will not crystallize due to the presently claimed compositions. Furthermore, the overabundance of water from syneresis can be addressed by the drying procedure discussed herein.

The present invention also provides a process of preparing stable soft gelatin capsules comprising water-insoluble ingredients and a crystallization inhibitor (as well as the other excipients mentioned herein). The process comprises enclosing the capsule contents in a gelatin shell, followed by drying the capsules using a stream of air at a temperature of between about 25, 30, 35, to 40° C. After drying, the process can further comprise dehydrating the gelatin capsules in an ethanol bath (e.g., anhydrous ethanol). The dehydrating can be performed in the presence of an anti-adhering additive to prevent the capsules from adhering to one another. Examples of anti-adhering additives include lecithin and triacyl glycerols, wherein the acyl portion has from 6, 7, 8, 9, 10, 11, 12, 13, 14, 15, 16, 17, to 18 carbon atoms.

Water-insoluble, as used herein, refers to an ingredient that requires the presence of an excipient to increase its solubility and therefore bioavailability to an acceptable level.

Active ingredient, as used herein, refers to a medicinal product, cosmetic product, food, or food additive that is desired to be administered to a patient in need thereof.

A water-insoluble active substance may be selected from non-limitative groups of adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic; antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor.

EXAMPLES

The following non-limitative examples are given to illustrate the present invention.

Example 1

Composition of the Contents of a Gelatin Capsule Containing a Lipophilic Immunosuppressive Agent

| | |
|---|---|
| Cyclosporine | 100 mg |
| Anhydrous ethanol | 120 mg |
| Macrogol 1100 glyceryl trioleate | 222 mg |
| Lecithin | 73 mg |
| Corn oil | 533 mg |
| Glyceryl monooleate | 60 mg |

Glyceryl monooleate was dissolved in corn oil and to this were added Macrogol, anhydrous ethanol, lecithin, and cyclosporine. This mixture was blended in an appropriate apparatus and filtered through a 5-μm cartridge filter. The solution so prepared was filed into oval 11 gelatin capsules and dried for about 60 minutes in a rotary (drum) drier with forced air flow at a temperature of 28° C. The pre-dried capsules were dehydrated for 5 minutes in 1% solution of lecithin in anhydrous ethanol. The capsules were placed in tray driers for 2 to 3 days, and finally packaged in aluminium blisters.

Example 2

Composition of the Contents of a Gelatin Capsule Containing a Lipophilic Immunosuppressive Agent

| | |
|---|---|
| Tacrolimus | 5 mg |
| Anhydrous ethanol | 15 mg |
| Polysorbate 80 | 50 mg |
| Lecithin | 15 mg |

| | |
|---|---|
| Miglyol 812 | 150 mg |
| Glyceryl monooleate | 15 mg |

Glyceryl monooleate was dissolved in Miglyol 812 and to this were added polysorbate, anhydrous ethanol, lecithin, and tacrolimus. The mixture was blended in an appropriate apparatus and filtered through a 5-μm cartridge filter. The solution was filled into oblong 5 gelatin capsules and dried for about 30 minutes in a rotary (drum) drier with forced air flow at a temperature of 30° C. The pre-dried capsules were dehydrated for 10 minutes in a mixture of triacylglycerols of 6, 7, 8, 9, 10, 11, 12, 13, 14, 5, 16, 17, to 18 carbon atoms and anhydrous ethanol. The capsules were placed in tray driers for 2 to 3 days and finally packaged in aluminium blisters.

Example 3

Comparison of the Robustness of a Placebo after the 5 w/w Addition of Various Emulsion Stabilizers The resistance of the contents of gelatin capsules to the water passing inside was quantified by performing a titration experiment. While stirring constantly using a magnetic stirrer at room temperature, the lipophilic contents intended for capsules was gradually titrated with water until the clear oily liquid begins to change into a milky turbid emulsion.

The robustness of the contents was expressed in the following table as an amount of water, in % w/w, necessary to induce emulsification of the contents.

| Emulsion stabilizer | Robustness (weight %) |
|---|---|
| Polysorbate 80 | 0.47 |
| Diglyceryl monooleate | 1.68 |
| Miglyol 812 | 0.57 |
| Decaglyceryl monooleate | 1.02 |
| Decaglyceryl monolaurate | 0.84 |
| Decaglyceryl decaoleate | 0.85 |
| Glyceryl monooleate | 4.98 |
| Glyceryl monolinoleate | 3.23 |

The above examples illustrate the increased resistance to water of a composition of the present invention compared with compositions absent a crystallization inhibitor. This increased resistance is expected to translate into enhanced stability of capsules.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A soft gelatin capsule, comprising:
   a. a gelatin shell and
   b. a capsule content comprising (1) a water-insoluble active ingredient dissolved in an excipient, and (2) a hydrophilic solvent comprising ethanol; and
   wherein the excipient comprises a crystallization inhibitor comprising a monoacylglycerol compound selected from glyceryl monooleate, glyceryl monolinoleate, glyceryl monopalmitate, glyceryl monostearate, glyceryl monolaurate, glyceryl monocaprylate, glyceryl monocaprate, and combinations thereof; and
   wherein the crystallization inhibitor is present in an amount of 2% to 10% w/w with respect to the weight of the capsule content.

2. The capsule of claim 1, wherein the crystallization inhibitor comprises two different monoacylglycerols.

3. The capsule of claim 1, wherein the excipient further comprises an oil.

4. The capsule of claim 3, wherein the oil is a vegetable oil.

5. The capsule of claim 4, wherein the vegetable oil is partially hydrophilized by the crystallization inhibitor.

6. The capsule of claim 1, wherein the excipient further comprises a lipophilic carrier and a surfactant.

7. The capsule of claim 6, wherein the lipophilic carrier is a di- or tri-ester of glycerol and a fatty acid or combination of fatty acids consisting of 6-18 carbon atoms.

8. The capsule of claim 6, wherein the excipient comprises no greater than 25% w/w of the hydrophilic solvent, no less than 20% w/w of the lipophilic carrier, and no greater than 50% w/w of the surfactant, wherein the surfactant has an HLB value greater than 11 and the lipophilic carrier is a di- or tri-ester of glycerol and a fatty acid or combination of fatty acids consisting of 6-18 carbon atoms.

9. The capsule of claim 6, further comprising a lipophilic solvent that is an oil.

10. The capsule of claim 6, wherein the surfactant is a glycerol macrogol ester.

11. The capsule of claim 6, wherein the excipient further comprises an antioxidant.

12. The capsule of claim 6, wherein the water-insoluble active ingredient is selected from the group consisting of: adrenergic agent; adrenocortical steroid; adrenocortical suppressant; aldosterone antagonist; amino acid; anabolic; analeptic; analgesic; anesthetic; anorectic; anti-acne agent; anti-adrenergic; anti-allergic; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic; antinauseant; antineoplastic; antineutropenic, antiparasitic; antiproliferative; antipsychotic; antirheumatic; antiseborrheic; antisecretory; antispasmodic; antithrombotic; anti-ulcerative; antiviral; appetite suppressant; blood glucose regulator; bone resorption inhibitor; bronchodilator; cardiovascular agent; cholinergic; depressant; diagnostic aid; diuretic; dopaminergic agent; estrogen receptor agonist; fibrinolytic; fluorescent agent; free oxygen radical scavenger; gastric acid supressant; gastrointestinal motility effector; glucocorticoid; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; psychotropic; radioactive agent; scabicide; sclerosing agent; sedative; sedative-hypnotic; selective adenosine A1 antagonist; serotonin antagonist; serotonin inhibitor; serotonin receptor antagonist; steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; and xanthine oxidase inhibitor.

13. A process for preparing the soft gelatin capsule of claim 1, said process comprising:
   i. enclosing the capsule content in the gelatin shell and
   ii. drying the resulting capsule with a stream of air at a temperature of 25-40° C.

14. The process of claim 13, further comprising:
   iii. dehydrating the capsules after drying in an ethanol bath in the presence of an anti-adhering additive.

15. The process of claim 14, wherein the ethanol is anhydrous and the anti-adhering additive is lecithin or a triacyl glycerol wherein the acyl portion of the triacyl glycerol is one or more fatty acid residues consisting of 6-18 carbon atoms.

16. The capsule of claim 1, wherein the monoacylglycerol compound is glyceryl mono-oleate.

17. The capsule of claim 1, wherein the monoacylglycerol compound is glyceryl monolinoleate.

18. The capsule of claim 6, wherein the monoacylglycerol compound is glyceryl mono-oleate.

19. The capsule of claim 6, wherein the monoacylglycerol compound is glyceryl monolinoleate.

20. The capsule of claim 1, wherein the monoacylglycerol compound is present in an amount of 5-10% w/w with respect to the weight of the capsule content.

21. The capsule of claim 6, wherein the monoacylglycerol compound is present in an amount of 5-10% w/w with respect to the weight of the capsule content.

* * * * *

UNITED STATES PATENT AND TRADEMARK OFFICE
CERTIFICATE OF CORRECTION

PATENT NO.       : 8,673,351 B2                             Page 1 of 1
APPLICATION NO. : 11/886500
DATED            : March 18, 2014
INVENTOR(S)      : Andrýsek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1323 days.

Signed and Sealed this
Twenty-ninth Day of September, 2015

Michelle K. Lee
*Director of the United States Patent and Trademark Office*